United States Patent
Kuhner et al.

(10) Patent No.: US 7,498,532 B2
(45) Date of Patent: Mar. 3, 2009

(54) CONTROL DEVICE FOR CONTROLLING ELECTROMEDICAL APPLIANCES

(75) Inventors: Ralf Kuhner, Stuttgart (DE); Roland Hundt, Neckartailfingen (DE)

(73) Assignee: ERBE Elektromedizin GmbH, Tubingen (DE)

( * ) Notice: Subject to any disclaimer, the term of this patent is extended or adjusted under 35 U.S.C. 154(b) by 149 days.

(21) Appl. No.: 10/578,579

(22) PCT Filed: Oct. 29, 2004

(86) PCT No.: PCT/EP2004/012261

§ 371 (c)(1),
(2), (4) Date: May 3, 2006

(87) PCT Pub. No.: WO2005/043569

PCT Pub. Date: May 12, 2005

(65) Prior Publication Data

US 2007/0078539 A1    Apr. 5, 2007

(30) Foreign Application Priority Data

Nov. 3, 2003    (DE)    ................ 103 51 199

(51) Int. Cl.
*H01H 3/14*    (2006.01)
(52) U.S. Cl. .................................. 200/86.5
(58) Field of Classification Search ........... 200/11 R, 200/51.02–51.06, 86.5; 74/512, 560–562; 307/119; 433/101, 113; 606/1, 32, 41, 126, 606/118; 378/63, 98, 115; 5/614, 616; 600/126, 600/118

See application file for complete search history.

(56) References Cited

U.S. PATENT DOCUMENTS

| | | | |
|---|---|---|---|
| 4,586,398 A * | 5/1986 | Yindra | 74/512 |
| 5,422,521 A * | 6/1995 | Neer et al. | 307/119 |
| 5,712,460 A | 1/1998 | Carr et al. | |
| 5,777,602 A | 7/1998 | Schaller et al. | |
| 5,787,760 A * | 8/1998 | Thorlakson | 74/512 |
| 5,883,615 A * | 3/1999 | Fago et al. | 345/156 |
| 6,017,354 A | 1/2000 | Culp et al. | |
| 6,051,797 A * | 4/2000 | Meinel | 200/86.5 |
| 6,150,951 A | 11/2000 | Olejniczak | |
| 6,280,436 B1 | 8/2001 | Freeman et al. | |
| 6,313,421 B1 * | 11/2001 | Abrahamsen | 200/332.1 |

(Continued)

FOREIGN PATENT DOCUMENTS

DE    41 25 313 A1    2/1993

(Continued)

Primary Examiner—Michael A Friedhofer
(74) Attorney, Agent, or Firm—Dickstein Shapiro LLP

(57) ABSTRACT

A known arrangement for controlling electromedical appliances or groups thereof employs foot-actuated switches or push-button switches, which are separately connected to each appliance. When it is necessary to control a large number of appliances or appliance groups, a large number of push-buttons or pedal switches is also required, the connections of which cause disturbances in the operating room. In the present invention the switching means or pedal switches are provided with connecting means by way of which the switching means can be connected to one another. Allocation means are provided in order to allocate to the control signals particular controlling functions with reference to the appliances or appliance groups. Information-transfer means transmit control signals from the switching means or pedal switches to the appliances or appliance groups.

7 Claims, 3 Drawing Sheets

U.S. PATENT DOCUMENTS

| | | | |
|---|---|---|---|
| 6,368,269 B1 * | 4/2002 | Lane | 600/126 |
| 6,452,123 B1 * | 9/2002 | Chen | 200/86.5 |
| 6,866,507 B2 * | 3/2005 | Beerstecher | 433/101 |
| 6,894,236 B2 * | 5/2005 | Chappuis | 200/86.5 |
| 7,012,203 B2 * | 3/2006 | Hanson et al. | 200/86.5 |
| 2002/0115917 A1 | 8/2002 | Honda et al. | |
| 2002/0156466 A1 | 10/2002 | Sakurai et al. | |

FOREIGN PATENT DOCUMENTS

| | | |
|---|---|---|
| DE | 197 30 456 A1 | 1/1999 |
| DE | 198 01 152 A1 | 7/1999 |
| DE | 102 21 787 A1 | 1/2003 |
| DE | 695 27 537 T2 | 3/2003 |
| DE | 203 12 016 U1 | 11/2003 |
| EP | 0 864 293 A1 | 9/1998 |
| EP | 1 217 640 A2 | 6/2002 |
| WO | 02/14970 A2 | 2/2002 |
| WO | 02/32354 A1 | 4/2002 |

* cited by examiner

CONTROL DEVICE FOR CONTROLLING ELECTROMEDICAL APPLIANCES

CROSS-REFERENCE TO RELATED APPLICATIONS

This application is a section 371 of International Application No. PCT/EP2004/012261, filed Oct. 29, 2004, which was published in the German language on May 12, 2005, under International Publication No. WO 2005/043569 A1 and the disclosure of which is incorporated herein by reference.

BACKGROUND OF THE INVENTION

The invention relates to a control device for controlling electromedical appliances or groups of such appliances.

In order to control electromedical appliances, such as HF generators, laser equipment, surgical instruments employing water jets or similar apparatus used in particular in an operating theater, it is necessary for switching means to be employed, in particular by the surgeon, to control the function of the attached appliances or groups thereof according to the momentary requirements. For example, to stop bleeding an APC (argon-plasma coagulation) instrument is used, in which case actuation of a pedal switch on one hand opens a valve in order to deliver argon to a probe (and thus to the treatment site) and on the other hand to drive an HF generator in such a way that a high-frequency current flows from an electrode in the probe to the tissue while ionizing the argon, so that the tissue is coagulated. With the same device another function can also be performed, for which purpose the HF generator is switched into another mode of operation. All these control functions can be initiated with one switch, but usually several switches, which are often designed to be pressed by hand or foot. When several such push-buttons or pedals are needed to control one or more appliances or groups thereof, each of these closed systems is connected to the associated appliances or groups thereof by means of a cable. Cable-free connections are also known, but even for these a special transmission pathway is assigned to each switching device. If it is desired for another function to be activatable at an appliance or group thereof, the appropriate switching means to support the function now desired must be newly installed, or another switching means must be appropriately altered and its connections rearranged. This is a complicated process.

Furthermore, in some circumstances a large number of cable connections are needed, and this situation causes a considerable disturbance of the surgical procedures being carried out in the foreground, owing to both mechanical interference ("stumbling" over the cables) and electromagnetic interference caused by the many cables and control leads together acting as antennae. The alternative of replacing the many cables by many radio links in turn causes a large number of electromagnetic disturbances.

BRIEF SUMMARY OF THE INVENTION

It is an object of the invention to provide a control device for controlling a plurality of electrochemical appliances that may include a group of said appliances that is versatile and structurally compact, with little possibility of disturbances.

This object is achieved by a control device for controlling a plurality of electromedical appliances that may include a group of said appliances that comprises at least two switching means generating control signals to control the appliances or groups thereof, connecting means disposed on the switching means for connecting the switching means to one another, allocation means adapted to allocate to the control signals particular controlling functions with respect to the appliances or groups thereof, and information-transfer means adapted to transmit the control signals from the switching means to the appliances or groups thereof.

The success of the invention resides in the fact that the switching means are no longer directly connected (and this includes even wireless connection of whatever kind) to the appliances or groups thereof, but rather the switching means are indirectly connected thereto by way of the allocation means, so that within the latter a particular control function, designed for particular functions of the appliances or groups thereof, can be allocated to each switching means. In this way the informational content, so to speak, of the signals produced by the switching means can be changed without altering the switching means themselves. This makes it possible not only to change the function of already installed control devices, but also to couple to one another as many control devices as desired, producing what amounts to a "keyboard", in which the "significance of the keys" can be determined by the operator according to what is required.

The connecting means comprise a data bus designed so that after a plurality of switching means have been connected to one another, the control signals of all switching means are available at the data bus. This ensures in a simple manner that all signals from the switching means are made available simultaneously.

Each of the switching means in this case comprises two signal couplers, in particular plug-and-socket connectors, connected to the data bus in such a way that when several switching means are connected to one another in series, at least one of the signal couplers can be used to connect the data bus to the information-transfer means. As a result, an unlimited number of switching means can be plugged together to form a "keyboard".

The information-transfer means can be connected to the appliances or groups thereof by way of a lead. Alternatively it is possible to equip the information-transfer means with at least one transmitter that can be connected to the switching means, and to provide at least one receiver connected to the appliances or groups thereof, for wireless transmission of the control signals. This eliminates the risk of "stumbling" over wires.

As described above, the switching means can be connected directly to one another. In the case of mechanical connection, a base plate can be provided onto which the switching means are set. Alternatively it is possible to equip the base plate with intermediate connection means, by way of which the switching means can be connected to one another. Within this base plate, furthermore, the transmitter and/or power supply or the like can be disposed. Preferably coding means are provided so that switching means can be identified by the appliances or groups thereof, so that the appliances can recognize "by themselves" the switching means allocated to them, and malfunctions or incorrect combinations can be ruled out.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

In the following description, the same reference numerals are used for identical parts or parts with identical actions.

DETAILED DESCRIPTION OF THE INVENTION

Figure 1:
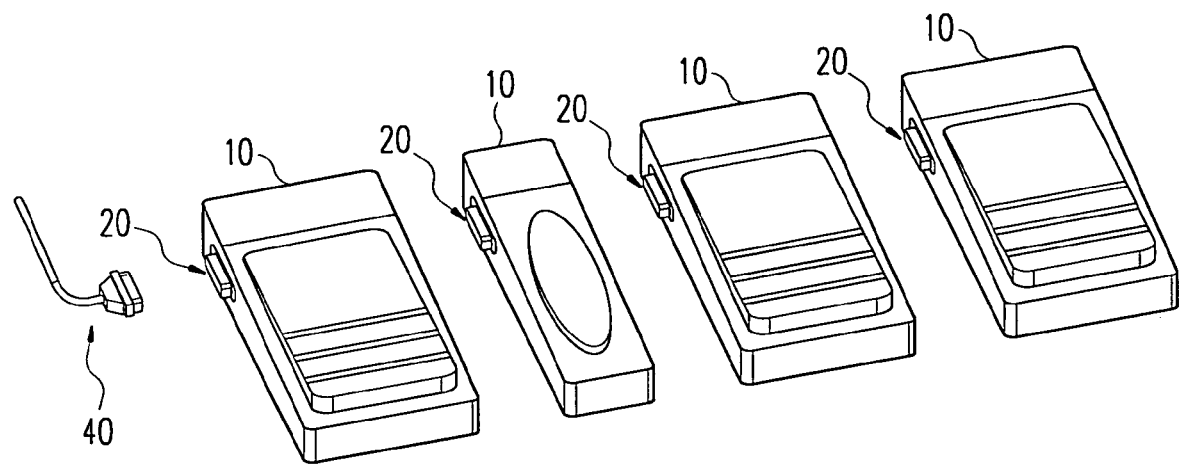
FIG. 1 shows a group of pedal switches separated from one another.
Figure 2:
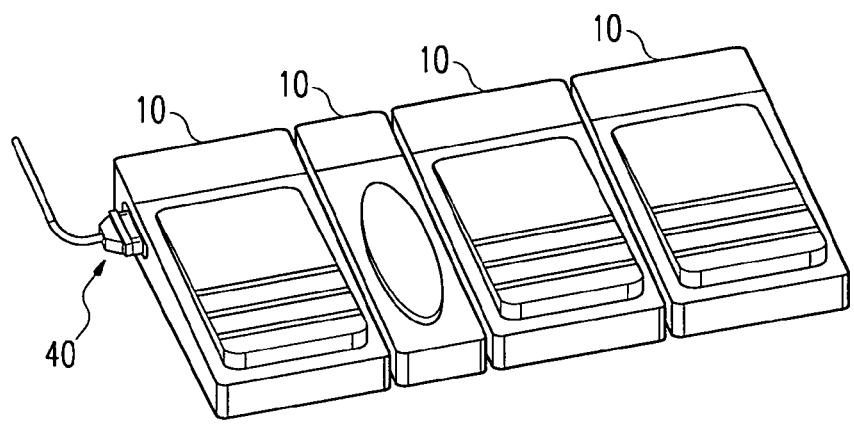
FIG. 2 shows the group of switches according to FIG. 1 when they have been plugged together.

As is evident in FIG. 1, a group of pedal switches 10 is provided, each of which comprises a multi-pole connecting means 20 and (on the opposite side of the housing, not shown) a corresponding connecting means, so that the switching means 10 shown here as pedal switches can be plugged together to form a group, as is shown in FIG. 2. In addition mechanical connections are provided so that the group shown in FIG. 2, which comprises a total of four pedal switches, is firmly interconnected mechanically and so can be manipulated as a unit. For connection to the appliances that are to be controlled, which are described in greater detail below, a cable is provided to serve as information-transfer means 40.

Figure 3:
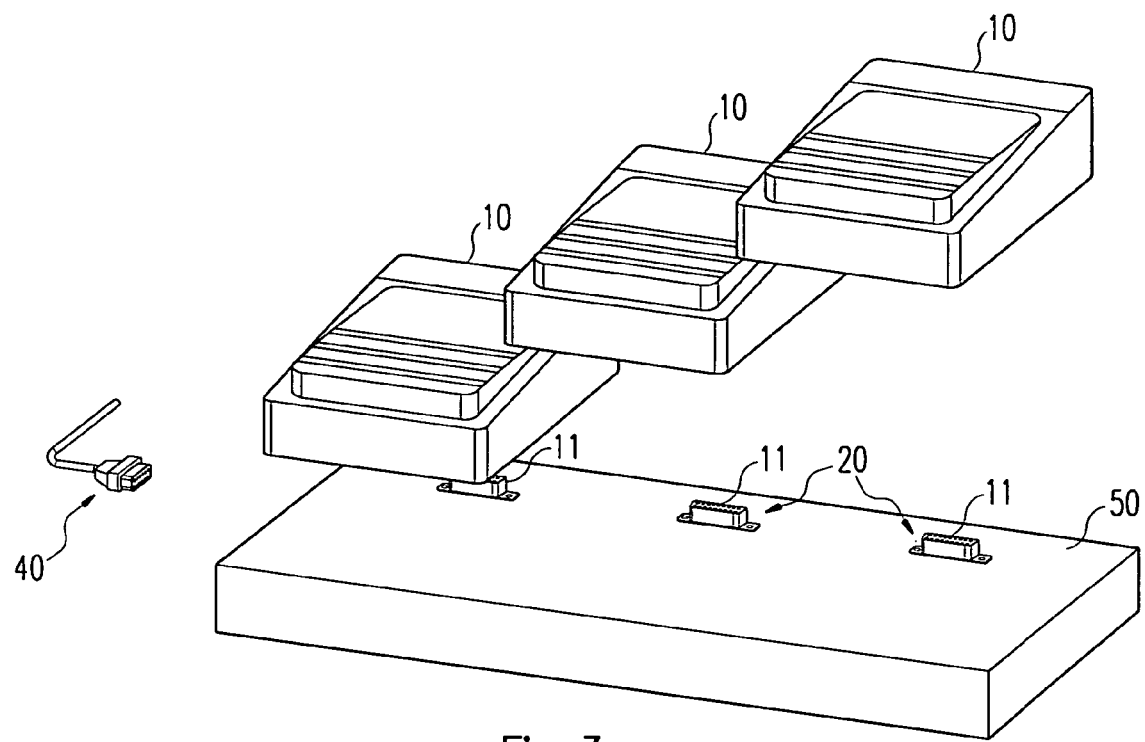
FIG. 3 shows a group of pedal switches with a base plate.

The embodiment shown in FIG. 3 differs from that according to FIG. 2 in that the pedal switches 10 are connected to one another not directly but indirectly, by way of associated plug connectors 11 in a base plate 50 that serves simultaneously as a pedestal for the group of pedal switches. Here, again, the connection to the appliances that are to be controlled is brought about by a cable 40.

Figure 4:
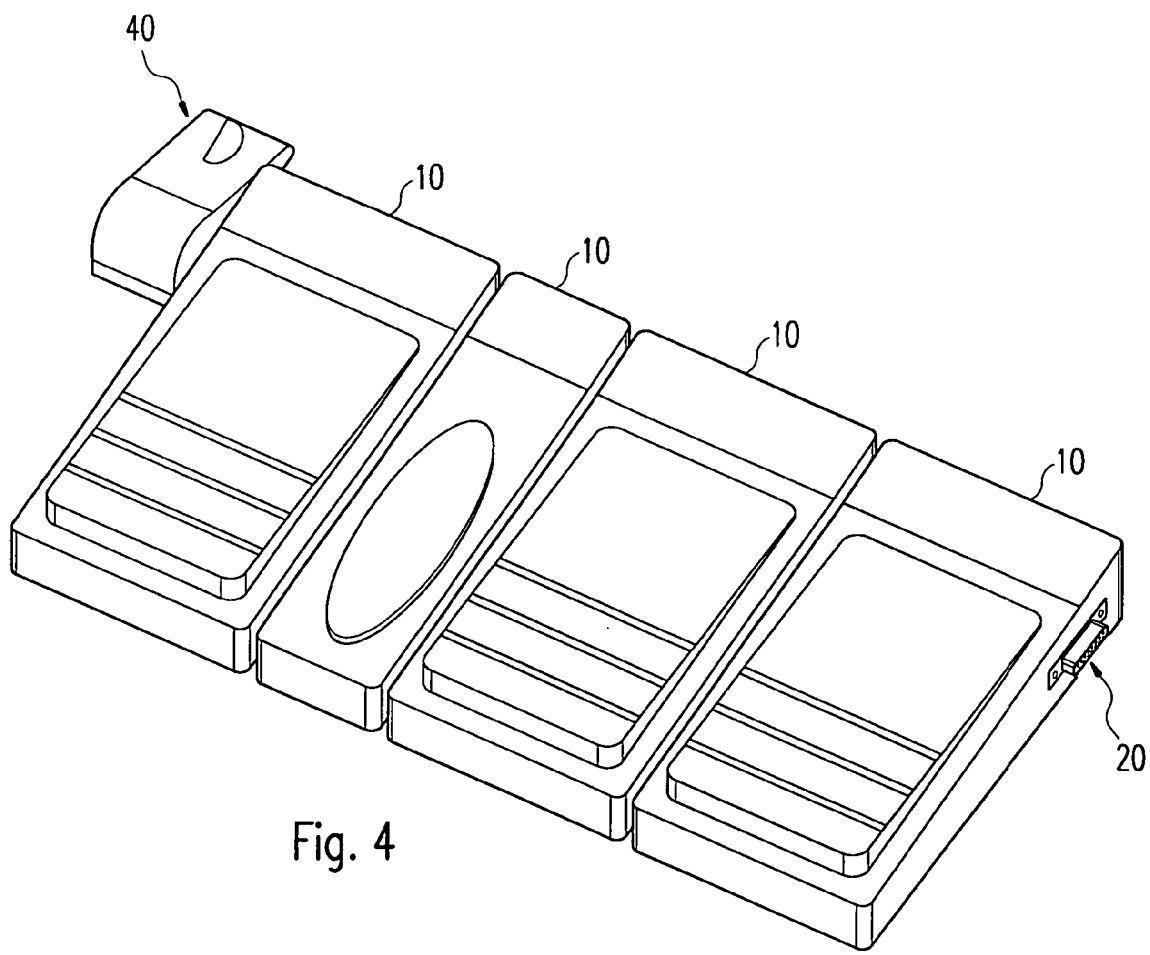
FIG. 4 shows a group of pedal switches with wireless connection.

The embodiment shown in FIG. 4 differs from that according to FIGS. 1 and 2 in that instead of a cable, the information-transfer means 40 is designed as a wireless transmitter, i.e. one that transmits by radio or infrared signals. Within these transmission means a rechargeable power source is also provided, so that the whole unit can easily be transported and set up at any desired sites, with no need for a cable to be attached. This embodiment, of course, can also be combined with that according to FIG. 3. In particular, for example, the wireless information-transfer means can be disposed within the base plate 50.

Figure 5:
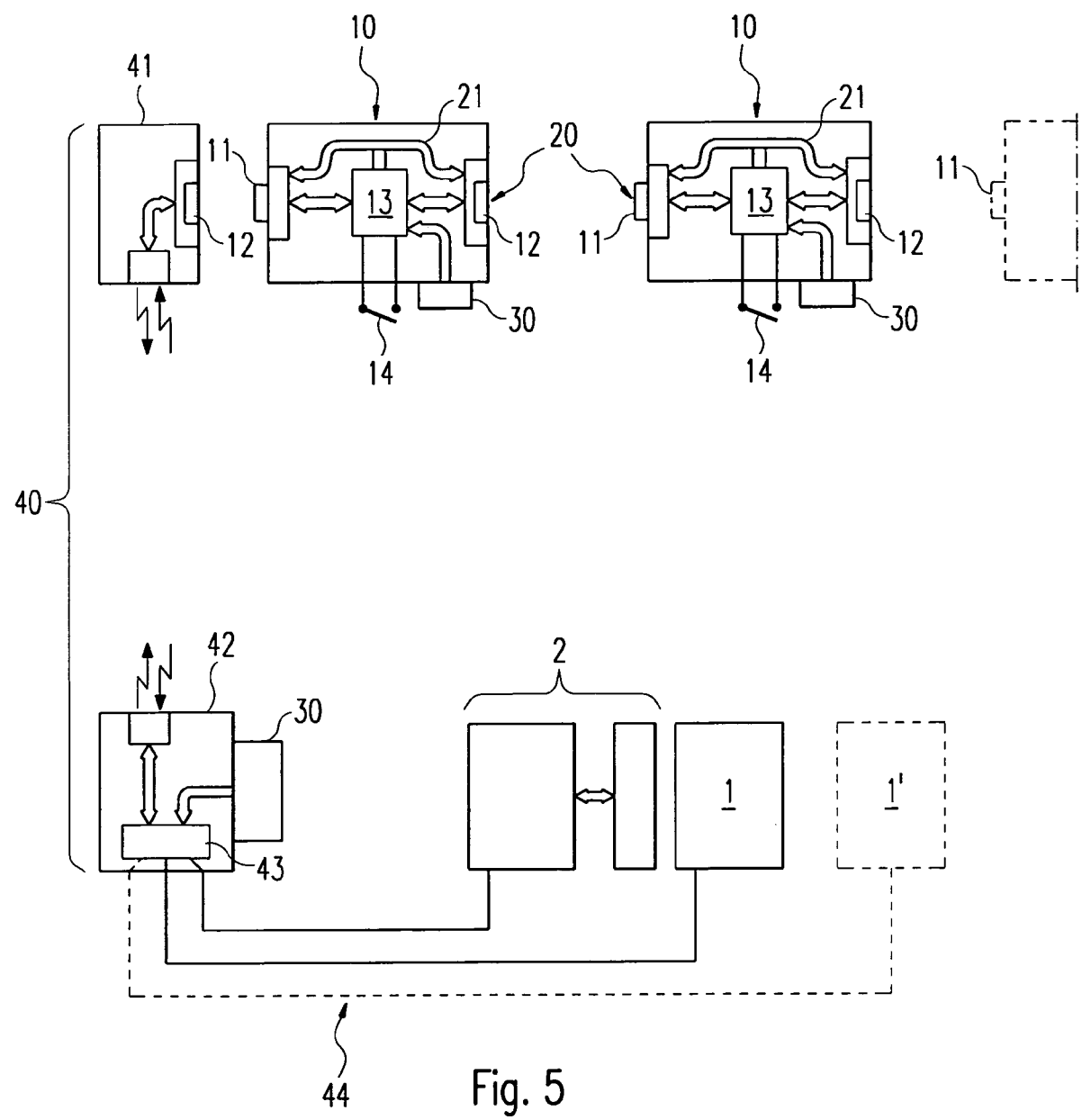
FIG. 5 is a schematic block diagram of one embodiment of the control device in accordance with the invention.

In FIG. 5 the electrical structure of the whole arrangement is shown in principle in a block diagram. It can be seen in this diagram that each of the switching means 10 comprises plug-and-socket connectors 11 and 12, which are correspondingly shaped so that an arbitrarily large number of switching means 10 can be arrayed side by side and electrically connected to one another. The information-transfer means 40 can then be plugged into the last (on the left, in FIG. 5) switching means 10.

One of the items provided in each of the switching means 10 is a data bus 21, which on one hand accepts the information arriving at the plug-and-socket connector 12 from another plugged-in switching means 10 and passes it on to the plug-and-socket connector 11 (and ultimately to the information-transfer means 40), and on the other hand is connected to a signal-generating means 13 so that by way of a switch 14, e.g. a pedal such as is shown in FIGS. 1-4, switch signals are generated and sent on to the plug-and-socket connector 11. At the switching means 10 there are additionally provided allocation means 30, e.g. in the form of coding switches, by way of which particular functions can be assigned to the various switching means 10, with reference to appliances 1, 1' or appliance groups 2, which are to be controlled by way of the switching means 10.

The items of information transferred within the data bus 21 are conducted through the connectors 11 and 12 to a transmitter 41, the signals from which are received by a receiver 42, which together with the transmitter 41 constitutes the information-transfer means 40. It should be pointed out that instead of a wireless transmission of this kind, a cable can be used.

The above-mentioned allocation means 30 can also be disposed within the receiver 42, so that for each switching means 10 the "content" of an item of switching information it has generated can also be sent on to a central site.

In addition, there is provided in the receiver 42 a coding means 43 designed so that the signals sent from the receiver 42 through the connecting cable 44 to the appliances 1, 1' or appliance groups 2 can carry out only the control functions that are permitted in those particular appliances or appliance groups. It is likewise possible to use such coding in order to block certain combinations of functions, so that for instance it is impossible during an operation for a given appliance to be used simultaneously for rinsing and for conducting high-frequency current, since such current should be switched on only in combination with the delivery of an inert gas, when no rinsing fluid is present. By this means, therefore, it is simultaneously possible to eliminate malfunction owing to errors made by the person operating the switching means 10.

It will be evident from the above that an essential point of the present invention resides in the fact that the switching means 10 are initially not specified for particular functions, and the allocation of functions (including protection against malfunctions) is brought about by the allocation means 30 and the coding means 43 (centrally or at each switching means 10).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. Control device for controlling a plurality of electromedical appliances that may include a group of said appliances comprising at least two switching means generating control signals to control said appliances, connecting means disposed on said switching means connecting said switching means to one another, allocation means adapted to allocate to said control signals particular controlling functions with reference to said appliances, and information-transfer means adapted to transmit said control signals from said switching means to said appliances.

2. Control device according to claim 1, wherein said connecting means comprise a data bus adapted such that when a plurality of said switching means are connected to one another, the control signals of all said switching means are available at said data bus.

3. Control device according to claim 2, wherein each of said switching means comprises two signal couplers that are connected to the data bus such that when said switching means are connected together in series, said data bus can be connected to said information-transfer means by means of at least one of the signal couplers.

4. Control device according to claim 1, wherein said information-transfer means comprise at least one transmitter connected to said switching means and at least one receiver connected to said appliances for wireless transmission of said control signals.

5. Control device according to claim 1, comprising a base plate on which said switching means is set.

6. Control device according to claim 5, wherein said base plate comprises intermediate connecting means to connect said switching means to one another.

7. Control device according to claim 1, comprising coding means that identify said switching means by the appliances.

* * * * *